United States Patent
Boiteux et al.

(10) Patent No.: US 7,293,989 B2
(45) Date of Patent: Nov. 13, 2007

(54) PERIODONTAL THERAPY INSTRUMENT

(75) Inventors: Philippe Boiteux, Arc et Senans (FR); Hubert Euvrard, Besancon (FR); Jean-Pierre Ouhayoun, Paris (FR)

(73) Assignee: Micro-Mega International Manufactures, Besancon (FR)

( * ) Notice: Subject to any disclaimer, the term of this patent is extended or adjusted under 35 U.S.C. 154(b) by 58 days.

(21) Appl. No.: 10/534,267

(22) PCT Filed: Oct. 29, 2003

(86) PCT No.: PCT/FR03/03218

§ 371 (c)(1),
(2), (4) Date: May 6, 2005

(87) PCT Pub. No.: WO2004/043283

PCT Pub. Date: May 27, 2004

(65) Prior Publication Data

US 2006/0035196 A1    Feb. 16, 2006

(30) Foreign Application Priority Data

Nov. 8, 2002    (FR) .................................. 02 13975

(51) Int. Cl.
*A61C 1/12* (2006.01)
*A61C 1/07* (2006.01)

(52) U.S. Cl. ........................................ 433/82; 433/119

(58) Field of Classification Search ................ 433/102, 433/118, 119, 165, 166, 82, 86, 85; 606/170; 604/22

See application file for complete search history.

(56) References Cited

U.S. PATENT DOCUMENTS

| 5,419,703 | A | * | 5/1995 | Warrin et al. ................ 433/216 |
| 5,531,597 | A | * | 7/1996 | Foulkes et al. ............. 433/119 |
| 5,725,370 | A | | 3/1998 | Himeno et al. |
| 5,816,808 | A | | 10/1998 | Gambarini et al. |
| 6,176,703 | B1 | | 1/2001 | Gugel et al. |
| 6,312,256 | B1 | | 11/2001 | Dieras et al. |
| 6,379,371 | B1 | * | 4/2002 | Novak et al. ................ 606/169 |
| 2004/0023187 | A1 | * | 2/2004 | Hickok ........................ 433/119 |
| 2004/0234924 | A1 | * | 11/2004 | Hickok et al. .............. 433/119 |
| 2004/0241608 | A1 | * | 12/2004 | Hickok ........................ 433/119 |

FOREIGN PATENT DOCUMENTS

| EP | 0715508 | 6/1996 |
| WO | WO 9535068 | 12/1995 |

* cited by examiner

*Primary Examiner*—Cary E. O'Connor
(74) *Attorney, Agent, or Firm*—Gary M. Cohen

(57) ABSTRACT

An instrument for periodontal treatment includes a blade (1) which is integrally connected to a head (2). The head (2) can be coupled to a handpiece to impart a vibratory movement to the blade (1). The blade (1) has an active part (1 *a*) distributed along the blade (1) on a side defined by a plane passing through the axis of the blade (1). The center of the blade (1) is additionally provided with an irrigation channel (4) for receiving a liquid which opens out at the center of the active part (1 *a*) of the blade (1) along the major part of its length. This ensures, on the one hand, cleaning of the active part (1 *a*) of the tool during a procedure, and on the other hand, removal of the detached particles.

11 Claims, 2 Drawing Sheets

PERIODONTAL THERAPY INSTRUMENT

The present invention relates to an instrument for periodontal treatment and more particularly to an instrument permitting scaling and root surface treatment for the purpose of cleaning the periodontal pockets.

Such instruments consisting of manual curettes, or of inserts mounted on vibratory handpieces, are already known at present. However, the rigidity of the existing instruments does not permit treatment of the periodontal pockets or satisfactory cleaning of the furcations, thus forcing the practitioner to practice traditional methods of periodontal surgery involving cutting of flaps.

An instrument with which it is possible to overcome the aforementioned disadvantages is also known in particular from the patent EP 0 715 508 B1 filed by the present Applicant. This instrument comprises a shank and a blade; the latter has an active part with two sectors distributed along the blade and each situated on either side of a plane passing through the axis of the blade. These two sectors have different levels of aggressiveness, with the result that, during treatment, with the instrument introduced into the periodontal pocket, the more aggressive sector comes into contact with the root surface of the tooth, and the less aggressive sector comes into contact with the mucosa. Said blade is held, by way of its shank, on a handpiece which imparts a vibratory movement to it in order to allow both sectors to detach the tartar to be removed.

Although such an instrument is satisfactory, it continues to be the subject of refinements aimed at improving comfort for patient and practitioner alike.

To this end, the subject of the present invention is an instrument for periodontal treatment, comprising a blade connected integrally to a head intended to be coupled to a handpiece so as to impart to said blade a vibratory movement, said blade having, on one of the sides delimited by a plane passing through its axis, an active part distributed along the blade, characterized in that said blade is additionally provided with an irrigation channel for liquid arranged at its center, this channel opening out at the center of the active part of said blade along the major part of its length, thus ensuring, on the one hand, cleaning of the active part of the tool during the procedure, and, on the other hand, removal of the detached particles.

According to an advantageous characteristic of the present invention, said blade is provided with a plane intersecting with said channel and thus providing the opening of the channel on the active part, and this plane of intersection is inclined with respect to the axis and defines the active part of the blade on which is arranged, on each side of the opening of the channel, a plurality of notches or any other similar configuration affording a surface roughness adequate for its use.

According to one embodiment variant, the end of the blade has a curvature.

According to another embodiment variant, the end of the blade is able to be curved by the practitioner for adapting it to the particular case being treated, for example for access to the furcations.

Still according to the invention, the blade is mounted in an articulated manner on said head, for example by means of a hinge of the ball-and-socket type, thus affording the possibility of orienting the position of the active part of the blade with respect to the grip of the apparatus.

According to an embodiment variant, the end remote from the free part of said blade is provided with a means for detachable fixation to the head.

According to one embodiment, this means for detachable fixation of the blade comprises a bushing which can be maneuvered in particular by the practitioner and on which the blade is connected integrally, and this bushing is additionally provided with an annular groove which, in the mounted position on said head, forms a leaktight annular chamber for communication between the irrigation channel of the blade and a delivery channel for liquid arranged on the head.

According to another advantageous characteristic of the invention, said head is provided with a channel for delivery of liquid which is linked to the irrigation channel of the blade.

According to yet another advantageous characteristic of the invention, the entry point of the liquid is external or internal to the handpiece.

The abovementioned characteristics of the invention, and others too, will appear more clearly on reading the following description of an illustrative embodiment, with reference to the attached drawings, in which:

FIG. 1 is a side view of an instrument according to the present invention, and

FIG. 2 is a view similar to FIG. 1, illustrating an embodiment variant of the present invention.

FIG. 1 depicts an instrument for dental surgery, in particular an instrument for periodontal treatment, comprising a blade 1, also designated as an insert, connected integrally to a head 2 which is coupled removably and interchangeably to a handpiece (not shown).

According to the embodiment shown, said blade 1 has a circular cross section and, on one of the sides delimited by a plane passing through the axis of the blade, it has an active part 1a distributed along said blade.

This active part 1a is made up of a plurality of notches 3 projecting from the blade and arranged on parallel planes, thus giving it the desired surface roughness. Thus, during treatment, with the instrument introduced into the periodontal pocket, the active part 1a of the blade (that is to say the part provided with a surface roughness) comes into contact with the root surface of the tooth, and the other part 1b of the blade, that is to say the less aggressive part or even smooth part, comes into contact with the mucosa.

It will be noted that these planes can be inclined with respect to the plane perpendicular to the axis of the instrument in order to ensure greater efficacy of the blade.

According to the present invention, said blade 1 is provided with an irrigation channel 4 for liquid arranged at its center, this channel 4 opening out at the center of the active part 1a of said blade 1 along the major part of its length, thus ensuring, on the one hand, cleaning of the active part of the tool during the procedure and, on the other hand, removal of the detached particles, as is explained in greater detail below.

According to a preferred embodiment of the invention, in order to provide the opening 5 of the channel 4 on the active part 1a, said blade 1 is provided with a plane 6 intersecting with said channel 4. This plane of intersection 6 is advantageously inclined with respect to the axis and defines the active part 1a of the blade 1 on which is arranged, on each side of the opening of the channel, the plurality of notches 3 or any other similar configuration providing a surface roughness adequate for its use.

The end remote from the free part of said blade 1 is provided with a means for detachable fixation to the head.

According to one embodiment, this means of fixation is composed of a bushing 7 which can be maneuvered in particular by the practitioner and on which the blade is integrally connected in order to allow it to be detached from the head and make it interchangeable.

This bushing 7 is additionally provided with an annular groove 8 which, in the mounted position on said head 2, forms an annular chamber 9 rendered leaktight by the provision, on either side of said chamber 9, of a sealing member 10 and 11, as is illustrated in FIG. 1.

This annular chamber 9 provides the communication between the irrigation channel 4 of the blade 1 and a delivery channel 12 for liquid such as water, disinfectant or any other product intended principally to irrigate the tissues during treatment, said delivery channel 12 being arranged on the head 2.

It will be noted that the entry point of the liquid may be external to the handpiece, as is illustrated in FIG. 1, or internal to the handpiece.

Said head 2 is mounted preferably on an ultrasound-generating apparatus whose ultrasonic vibrations have intrinsic antibacterial properties. Also, by virtue of these vibrations, said blade 1 is able to reach and file the tooth, without damaging the residual connective tissue surrounding it.

The way in which the instrument for periodontal treatment according to the invention is used will already be evident from the above description.

The practitioner mounts the instrument onto a handpiece and connects the delivery channel 12 for liquid to an entry point, then places the face of the active part 1a in contact with the root surface of the tooth.

The vibration of the instrument thus brings about removal of the granulated tissue of the mucous wall of the periodontal alveolus, and surface treatment of the root. Direct irrigation on the blade, by way of the channel 4, permits removal of the debris and thus better visibility of the site for the practitioner.

It will be noted that the end of the blade 1 can be pre-curved or can be manually shaped by the practitioner, depending on the anatomy of the tooth to be treated, additionally making it possible to penetrate the pockets atraumatically, but also to more effectively clean plane root surfaces inside larger alveoli.

It will be noted that the length of the blade 1 is similar to that of the known endodontic files, that is to say of the order of 12 to 25 mm and with a thickness of the order of 0.1 to 3 mm.

FIG. 2 shows an embodiment variant of the instrument for periodontal treatment in which the bushing 7 does not pass through said head 2, thus affording the advantage of reducing the number of sealing members to a single sealing member 13.

According to an embodiment variant not shown here, the blade 1 of the instrument is mounted in an articulated manner on the head, for example by means of a hinge of the ball-and-socket type, thus affording the possibility of orienting the position of the active part of the blade with respect to the grip of the apparatus.

From reading the above description, it will be appreciated that the instrument for periodontal treatment according to the present invention is relatively simple to produce and permits treatment that is rapid and atraumatic for the patient. In addition, this is an instrument which does not require a surgical intervention, in contrast to procedures with curettes which, for deep periodontal pockets, require cutting of flaps.

Although the invention has been described in connection with two particular embodiments, it includes all technical equivalents of the means described.

Thus, for example, the shape of the blade which, instead of the optimal straight shape, could be narrowed in the direction of the tip in order to adapt it to use inside gingival alveoli. Likewise, the blade 1 can have any suitable cross section, for example elliptic.

Likewise, it will be noted that the instrument for periodontal treatment according to the invention may, if appropriate, be disposable.

The invention claimed is:

1. An instrument for periodontal treatment, comprising:
   a blade integrally connected to a head which is connectable to a handpiece for imparting vibratory movement to the blade;
   wherein the blade has a center defining an axis, wherein a plane passing through the axis defines opposing sides of the blade and wherein the blade has an active part distributed along the blade on one of the sides, and an irrigation channel provided in the center of the blade for receiving a liquid, wherein the channel opens out into the active part of the blade for ensuring cleaning of the active part of the instrument during a treatment procedure and a removal of detached particles; and
   wherein the blade has an end remote from the active cart of the blade, wherein the end of the blade is detachably fixed to the head by a maneuverable bushing, wherein the blade is integrally connected on the bushing, and wherein the bushing includes an annular groove which, when the bushing is mounted on the head, forms a leak-tight annular chamber for ensuring communication between the irrigation channel of the blade and a delivery channel on the head for receiving liquid.

2. The instrument of claim 1 wherein the active part of the blade has a length, and a center along major portions of the length of the active part of the blade, and wherein the channel opens out at the center of the active part of the blade.

3. The instrument of claim 1 wherein the plane is inclined with respect to the axis, wherein the plane defines the active part of the blade and intersects with the channel, and wherein an opening is provided in the channel along the active part of the blade where the plane intersects with the channel.

4. The instrument of claim 3 wherein a surface roughness is provided on opposing sides of the opening of the channel.

5. The instrument of claim 4 wherein the surface roughness is a plurality of notches.

6. The instrument of claim 1 wherein the active part of the blade has an end which is capable of receiving a curvature applied by a practitioner.

7. The instrument of claim 1 wherein the delivery channel on the head is coupled with the irrigation channel of the blade, for delivering the liquid to the irrigation channel.

8. The instrument of claim 7 wherein the channel for delivering the liquid has an entry point which is external to the handpiece.

9. The instrument of claim 7 wherein the channel for delivering the liquid has an entry point which is internal to the handpiece.

10. The instrument of claim 1 wherein the instrument is disposable.

11. The instrument of claim 1 wherein the bushing includes a notched cap extending from the head, for maneuvering the bushing relative to the head.

* * * * *

UNITED STATES PATENT AND TRADEMARK OFFICE
CERTIFICATE OF CORRECTION

| | |
|---|---|
| PATENT NO. | : 7,293,989 B2 |
| APPLICATION NO. | : 10/534267 |
| DATED | : November 13, 2007 |
| INVENTOR(S) | : Philippe Boiteux et al. |

It is certified that error appears in the above-identified patent and that said Letters Patent is hereby corrected as shown below:

Column 1, line 3 through Column 4, line 8 should read:
--BACKGROUND OF THE INVENTION The present invention relates to an instrument for periodontal treatment, and more particularly, to an instrument which permits scaling and root surface treatment for the purpose of cleaning periodontal pockets.

Instruments of this type, such as manual curettes, or inserts mounted on vibratory handpieces, are already known. However, the rigidity of the known instruments does not permit treatment of the periodontal pockets, or satisfactory cleaning of the furcations, thereby forcing the practitioner to use traditional methods of periodontal surgery involving the cutting of flaps.

An instrument which has made it possible to overcome the aforementioned disadvantages is also known, in particular, from EP 0 715 508 B1. The disclosed instrument comprises a shank and a blade. The blade has an active part with two sectors distributed along the blade, each of which is situated on either side of a plane passing through the axis of the blade, and the two sectors have different levels of aggressiveness. As a result, during treatment and with the instrument introduced into the periodontal pocket, the more aggressive sector comes into contact with the root surface of the tooth, and the less aggressive sector comes into contact with the mucosa. The blade is held, by way of its shank, on a handpiece which imparts a vibratory movement to the blade in order to allow both sectors to detach tartar to be removed.

Although the disclosed instrument is satisfactory, it continues to be the subject of refinements for improving the comfort for both the patient and the practitioner.

SUMMARY OF THE INVENTION

To this end, and in accordance with the present invention, an instrument for periodontal treatment is provided which comprises a blade integrally connected to a head for coupling the blade to a handpiece so as to impart a vibratory movement to the blade. An active part is distributed along the blade on a side of the blade which is defined by a plane passing through the axis of the blade. The blade is additionally provided with an irrigation channel for liquid, arranged at the center of the blade. The channel opens out at the center of the active part of the blade, along the major part of its length, to ensure, on the one hand, cleaning of the active part of the tool during a procedure and, on the other hand, removal of the detached particles.

UNITED STATES PATENT AND TRADEMARK OFFICE
CERTIFICATE OF CORRECTION

| | |
|---|---|
| PATENT NO. | : 7,293,989 B2 |
| APPLICATION NO. | : 10/534267 |
| DATED | : November 13, 2007 |
| INVENTOR(S) | : Philippe Boiteux et al. |

It is certified that error appears in the above-identified patent and that said Letters Patent is hereby corrected as shown below:

In accordance with the present invention, the blade is advantageously provided with a plane which intersects with the channel, thereby providing an opening for the channel on the active part. The intersecting plane is inclined with respect to the axis of the blade and defines the active part of the blade. A plurality of notches, or some other similar configuration, is arranged on each side of the opening of the channel to provide a surface roughness which is adequate for use of the blade.

Various alternative embodiments of the instrument of the present invention can be provided.

For example, in one alternative embodiment, the end of the blade has a curvature. In another alternative embodiment, the end of the blade can be curved by the practitioner for adapting the blade to the particular treatment which is being performed, for example, for access to the furcations.

Further in accordance with the present invention, the blade is mounted on the head in an articulated manner, for example, by means of a hinge of the ball-and-socket type. This allows the position of the active part of the blade to be oriented with respect to the grip of the apparatus.

In another alternative embodiment, the end remote from the active part of the blade is provided with a means for detachable fixation to the head of the instrument. For example, such detachable fixation of the blade can be accomplished with a bushing which can be maneuvered, in particular, by the practitioner. The blade is then integrally connected on the bushing. The bushing is additionally provided with an annular groove which, in a position mounted on the head, forms a leak-tight annular chamber for communication between the irrigation channel of the blade and a delivery channel for liquid arranged on the head.

The head is advantageously provided with a channel for the delivery of liquid which is linked to the irrigation channel of the blade. The entry point for the liquid can be external or internal to the handpiece.

The above-mentioned characteristics of the present invention, in addition to other characteristics which will become apparent to the person of ordinary skill, are discussed in the detailed description of illustrative embodiments which is provided hereafter, with reference to the following drawings.

UNITED STATES PATENT AND TRADEMARK OFFICE
CERTIFICATE OF CORRECTION

PATENT NO.        : 7,293,989 B2
APPLICATION NO.   : 10/534267
DATED             : November 13, 2007
INVENTOR(S)       : Philippe Boiteux et al.

It is certified that error appears in the above-identified patent and that said Letters Patent is hereby corrected as shown below:

DETAILED DESCRIPTION OF PREFERRED EMBODIMENTS

Figure 1:
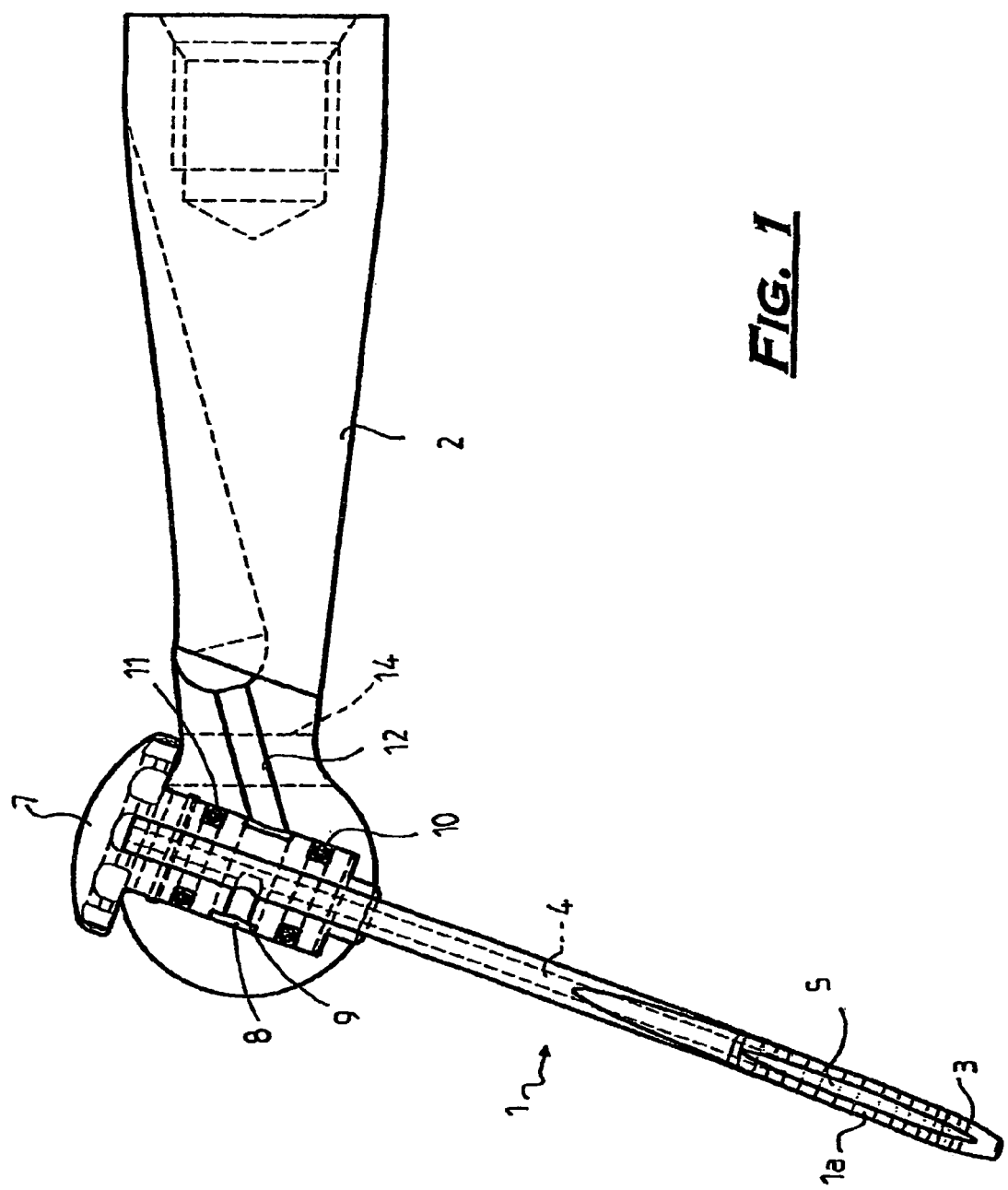
Figure 1 is a side view of an instrument of the present invention.

Figure 1 shows an instrument for dental surgery, in particular, an instrument for periodontal treatment. The illustrated instrument comprises a blade 1, which is also referred to as an insert, integrally connected to a head
2. The head 2 is removably and interchangeably coupled to a handpiece (not shown).

In the embodiment shown, the blade 1 has a circular cross-section. An active part 1a of the blade 1 is distributed along a side of the blade which is defined by a plane passing through the axis of the blade.

The active part 1a is made up of a plurality of notches 3 which project from the blade and which are arranged on parallel planes, thereby giving the active part 1a the desired surface roughness. Thus, during a treatment and with the instrument introduced into a periodontal pocket, the active part 1a of the blade 1, i.e., the part provided with a surface roughness, comes into contact with the root surface of the tooth. An opposing part 1b of the blade (shown in Figure 2), i.e., a less aggressive part or even a smooth part, comes into contact with the mucosa. It will be noted that the parallel planes can be inclined with respect to the plane which defines the active part 1a of the blade 1, perpendicular to the axis of the instrument, in order to ensure greater efficacy of the blade.

In accordance with the present invention, the blade 1 is provided with an irrigation channel 4 for receiving a liquid. The channel 4 is arranged at the center of the blade 1, and opens out at the center of the active part 1a of the blade 1 along the major part of its length. This ensures, on the one hand, cleaning of the active part of the tool during a procedure and, on the other hand, the removal of detached particles, as is explained in greater detail below.

In a preferred embodiment of the present invention, the blade 1 is provided with a plane 6 which intersects with the channel 4 in order to provide the opening 5 of the channel 4 on the active part 1a. This plane of intersection 6 is advantageously inclined with respect to the axis of the blade 1 and defines the active part 1a of the blade 1. The previously described notches 3 (or other similar configuration) are arranged on each side of the opening 5 of the channel 4, providing a surface roughness adequate for use of the instrument.

The end remote from the active part of the blade 1 is provided with a means for detachable fixation to the head. In the embodiment shown, such detachable fixation is accomplished with a bushing 7 which can be maneuvered, in particular, by the practitioner. The blade is integrally connected on the bushing 7 in order to allow the blade 1 to be detached from the head, thereby making the blade interchangeable.

UNITED STATES PATENT AND TRADEMARK OFFICE
CERTIFICATE OF CORRECTION

| | |
|---|---|
| PATENT NO. | : 7,293,989 B2 |
| APPLICATION NO. | : 10/534267 |
| DATED | : November 13, 2007 |
| INVENTOR(S) | : Philippe Boiteux et al. |

It is certified that error appears in the above-identified patent and that said Letters Patent is hereby corrected as shown below:

The bushing 7 is additionally provided with an annular groove 8 which, when mounted on the head 2, forms an annular chamber 9. Sealing members 10, 11 are provided on either side of the chamber 9, as is illustrated in Figure 1, for making the annular chamber 9 leak-tight. The annular chamber 9 provides communication between the irrigation channel 4 of the blade 1 and a delivery channel 12 arranged on the head 2. The delivery channel 12 is provided for receiving a liquid such as water, a disinfectant or any other product which is principally intended for irrigating tissues during treatment. It will be noted that the entry point of the liquid can be external to the handpiece, as is illustrated in Figure 1, or internal to the handpiece (not shown).

The head 2 is preferably mounted on an ultrasound-generating apparatus whose ultrasonic vibrations have intrinsic antibacterial properties. Also, by virtue of such vibrations, the blade 1 is able to reach and file the tooth without damaging the residual connective tissue surrounding the tooth.

Use of the instrument of the present invention for performing periodontal treatments will be evident from the above description. The practitioner mounts the instrument onto a handpiece and connects the delivery channel 12 for receiving a desired liquid to an entry point. The face of the active part 1a is then placed in contact with the root surface of the tooth. Vibration of the instrument then brings about a removal of the granulated tissue of the mucous wall of the periodontal alveolus, and surface treatment of the root. Direct irrigation on the blade 1, using the channel 4, permits removal of the resulting debris, providing better visibility of the site for the practitioner.

The end of the blade 1 can be pre-curved, or can be manually shaped by the practitioner, depending on the anatomy of the tooth to be treated. This additionally makes it possible to penetrate the pockets atraumatically, and to more effectively clean plane root surfaces inside larger alveoli.

It will be noted that the length of the blade 1 is similar to that of previously known endodontic files, for example, on the order of 12 to 25 mm in length and having a thickness on the order of 0.1 to 3.0 mm.

Figure 2:
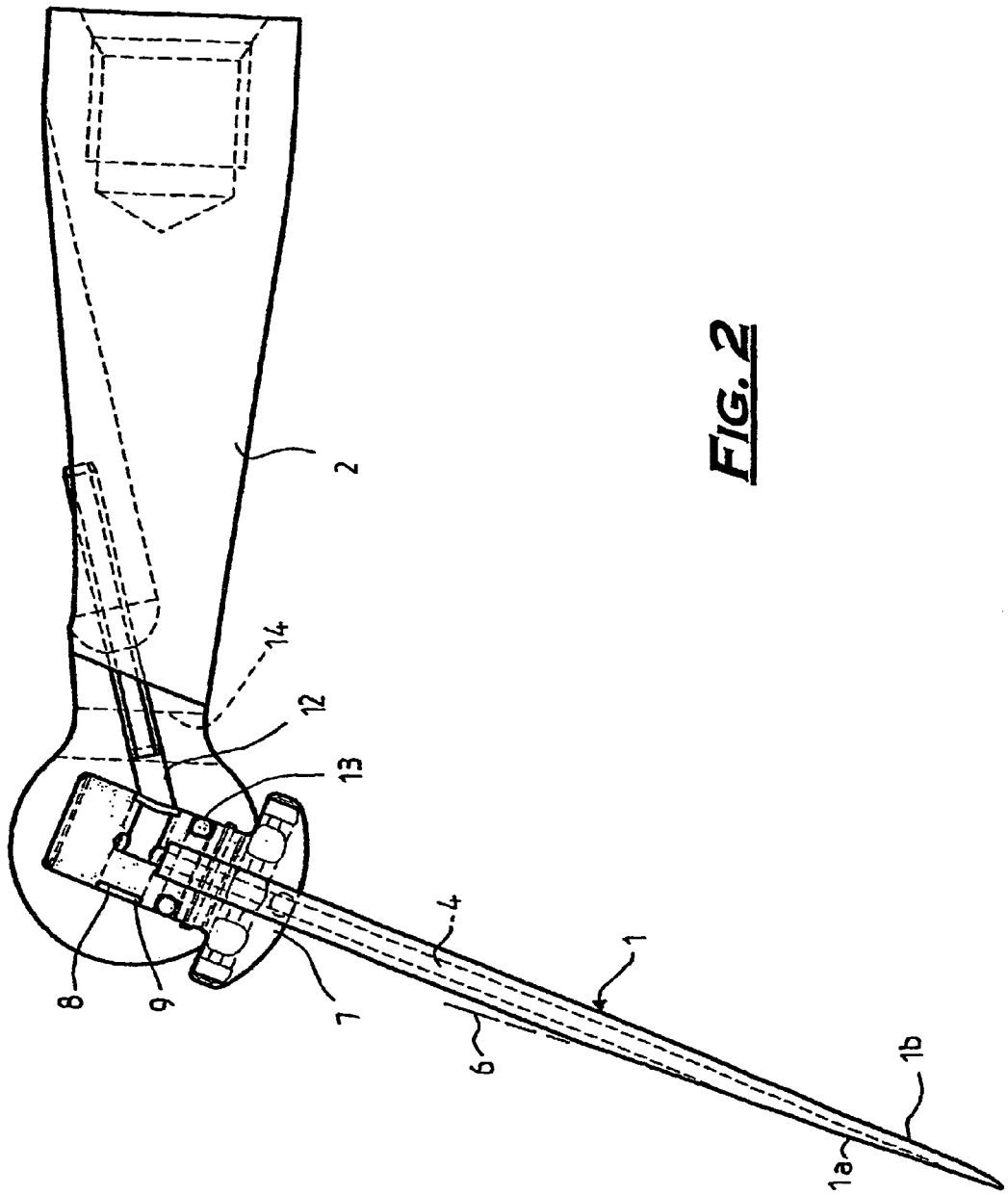
Figure 2 is a view similar to Figure 1, illustrating an alternative embodiment of the present invention.

Figure 2 shows an alternative embodiment of the instrument for periodontal treatment shown in Figure 1. In the alternative embodiment of Figure 2, the bushing 7 does not pass through the head 2, with the resulting advantage of reducing the number of sealing members to a single sealing member 13.

UNITED STATES PATENT AND TRADEMARK OFFICE
CERTIFICATE OF CORRECTION

PATENT NO. : 7,293,989 B2
APPLICATION NO. : 10/534267
DATED : November 13, 2007
INVENTOR(S) : Philippe Boiteux et al.

It is certified that error appears in the above-identified patent and that said Letters Patent is hereby corrected as shown below:

In yet another alternative embodiment, the blade 1 of the instrument is mounted on the head in an articulated manner, for example, by means of a hinge of the ball-and-socket type, as is schematically shown at 14. This affords the possibility of orienting the position of the active part of the blade with respect to the grip of the apparatus.

It will be appreciated from the foregoing description that the instrument for periodontal treatment of the present invention is relatively simple to produce and permits treatment that is rapid and atraumatic for the patient. In addition, the instrument does not require a surgical intervention, in contrast to procedures with curettes which, for deep periodontal pockets, require the cutting of flaps.

Although the present invention has been described in connection with two particular embodiments, it will be understood that the present invention also includes all technical equivalents of the described embodiments. For example, while the straight shape which has been described is considered optimal, the shape of the blade could instead be narrowed in the direction of the tip in order to adapt the blade for use inside gingival alveoli. Likewise, the blade can have any suitable cross-section, for example, an elliptical cross-section. It will further be noted that the instrument for periodontal treatment of the present invention can, if appropriate, be disposable.--

Signed and Sealed this

Ninth Day of September, 2008

JON W. DUDAS
*Director of the United States Patent and Trademark Office*